US011213341B2

(12) United States Patent
Garcia-Bengochea et al.

(10) Patent No.: US 11,213,341 B2
(45) Date of Patent: Jan. 4, 2022

(54) BOVIE ADAPTER FOR ROTATIONAL CONTROL AND FIXATION

(71) Applicant: JGMG BENGOCHEA, LLC, Jacksonville, FL (US)

(72) Inventors: Javier Garcia-Bengochea, Jacksonville, FL (US); John Souza, Sr., Monroe, NC (US)

(73) Assignee: JGMG BENGOCHEA, LLC, Jacksonville, FL (US)

(*) Notice: Subject to any disclaimer, the term of this patent is extended or adjusted under 35 U.S.C. 154(b) by 227 days.

(21) Appl. No.: 16/539,712

(22) Filed: Aug. 13, 2019

(65) Prior Publication Data
US 2020/0069360 A1 Mar. 5, 2020

Related U.S. Application Data

(60) Provisional application No. 62/718,272, filed on Aug. 13, 2018.

(51) Int. Cl.
*A61B 18/14* (2006.01)
*A61B 18/00* (2006.01)

(52) U.S. Cl.
CPC .... *A61B 18/14* (2013.01); *A61B 2018/00172* (2013.01)

(58) Field of Classification Search
CPC ............. A61B 18/14; A61B 18/1402; A61B 2018/0091; A61B 2018/00964; A61B 2018/1412; A61B 2018/1495; A61B 2018/00172; A61B 2090/035
USPC ........................................................ 606/45
See application file for complete search history.

(56) References Cited

U.S. PATENT DOCUMENTS

| 4,949,734 | A | * | 8/1990 | Bernstein ............... A61B 90/05 128/897 |
|---|---|---|---|---|
| 5,531,743 | A | | 7/1996 | Nettekoven et al. |
| 5,769,841 | A | | 6/1998 | Odell et al. |
| 5,836,960 | A | | 11/1998 | Kolesa et al. |
| 6,090,107 | A | | 7/2000 | Borgmeier et al. |
| 7,033,353 | B2 | | 4/2006 | Stoddard et al. |
| 7,503,917 | B2 | | 3/2009 | Sartor et al. |
| 7,686,803 | B2 | | 3/2010 | Mohan et al. |
| 8,177,784 | B2 | | 5/2012 | Van Wyk et al. |
| 8,231,621 | B2 | | 7/2012 | Hutchins et al. |
| 8,308,737 | B2 | | 11/2012 | Ryan |
| 8,348,944 | B2 | | 1/2013 | Van Wyk et al. |
| 8,449,540 | B2 | | 5/2013 | Sartor et al. |
| 8,486,064 | B2 | | 7/2013 | Van Wyk et al. |
| 9,138,284 | B2 | | 9/2015 | Krom et al. |
| 9,693,770 | B2 | | 7/2017 | Meade et al. |

(Continued)

FOREIGN PATENT DOCUMENTS

WO 2019104326 5/2019

*Primary Examiner* — Michael F Peffley
(74) *Attorney, Agent, or Firm* — McNees Wallace & Nurick LLC

(57) ABSTRACT

An adapter for an electrosurgical instrument includes a socket and a stabilizer extending from the socket. The socket includes a mounting surface having a geometry arranged and disposed to accept a distal end of the electrosurgical instrument, and at least one retaining surface, which arranged and disposed to interact with a conformation of the electrosurgical instrument when the socket is mounted onto the electrosurgical instrument such that the socket mounts non-rotatably.

20 Claims, 10 Drawing Sheets

(56) References Cited

U.S. PATENT DOCUMENTS

| | | |
|---|---|---|
| 9,743,977 B2 | 8/2017 | Smith et al. |
| 9,987,074 B2 | 6/2018 | Ineson |
| 10,039,594 B2 | 8/2018 | Krom et al. |
| 10,052,169 B2 | 8/2018 | Al-Jarba |
| 10,383,680 B2 | 8/2019 | Mark et al. |
| 10,595,936 B2 | 3/2020 | Zarins et al. |
| 10,631,917 B2 | 4/2020 | Ineson |
| 11,000,331 B2 | 5/2021 | Krom et al. |
| 2009/0062791 A1* | 3/2009 | Lee .................... A61B 18/1402 606/45 |
| 2009/0275939 A1 | 11/2009 | Mohan et al. |
| 2012/0123412 A1* | 5/2012 | Sartor ................ A61B 18/1402 606/45 |
| 2013/0079773 A1 | 3/2013 | Van Wyk et al. |
| 2015/0088132 A1* | 3/2015 | Minskoff ........... A61B 18/1402 606/49 |
| 2017/0156789 A1 | 6/2017 | Ravikumar et al. |
| 2017/0224413 A1 | 8/2017 | Ravikumar et al. |
| 2017/0333120 A1 | 11/2017 | Truckai |

* cited by examiner

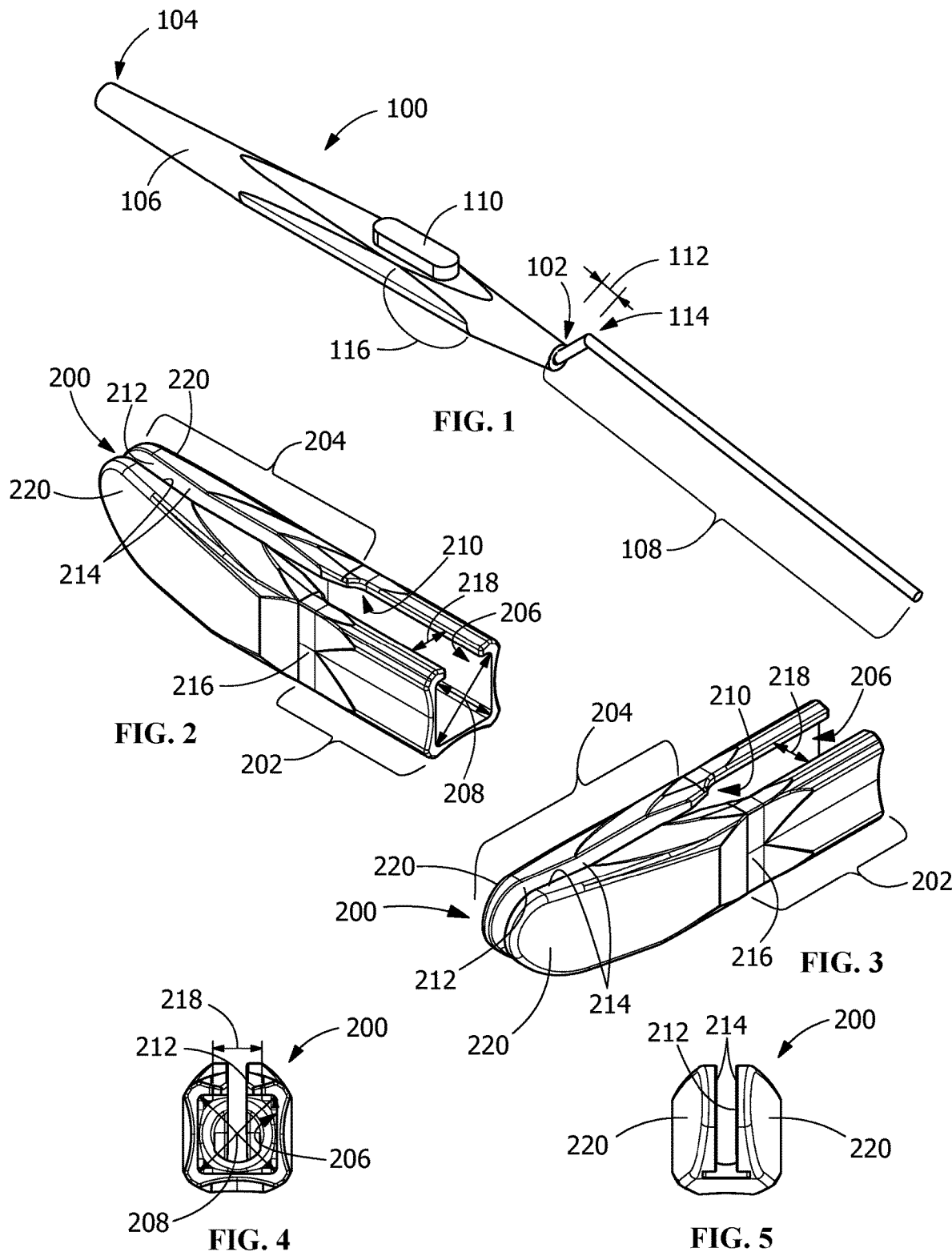

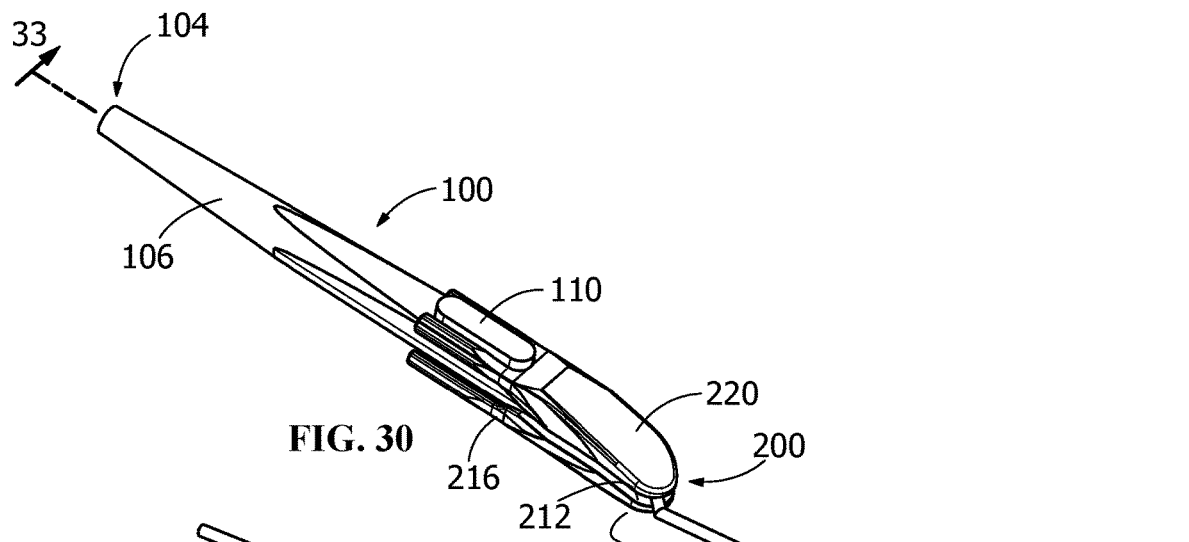
FIG. 30
FIG. 31
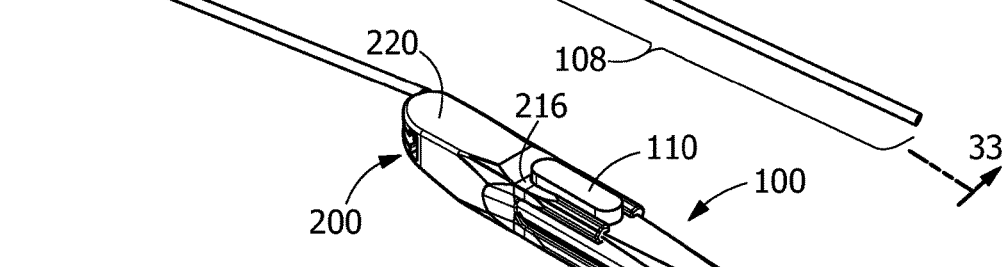
FIG. 32
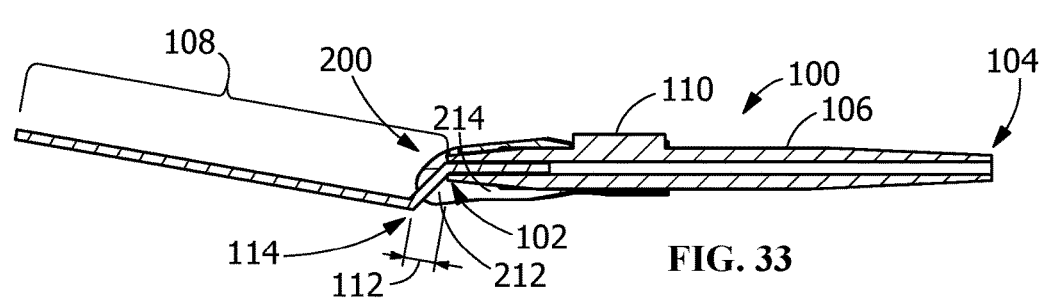
FIG. 33

BOVIE ADAPTER FOR ROTATIONAL CONTROL AND FIXATION

RELATED APPLICATIONS

This application claims the benefit of and priority to U.S. Prov. App. No. 62/718,272, entitled "Bovie Adapter for Rotational Control and Fixation," filed Aug. 13, 2018, which is hereby incorporated by reference in its entirety.

FIELD OF THE INVENTION

The present application describes adapters for electrosurgical instruments. More particularly, the present application describes adapters for electrosurgical instruments which restrict rotation of an elongate electrosurgical member.

BACKGROUND OF THE INVENTION

Electrosurgical probes, typically referred to as "bovies," provide the dual utility of mechanical manipulation of materials and tissue, and application monopolar electrical current to provide a high-frequency alternating polarity to tissue for purposes of cutting, coagulating, dissecting, or fulgurating tissue. Such devices are well known in the art, and typically include an elongate electrosurgical member that emits an electrical current at its distal tip. The electrosurgical member is affixed at its proximal end to a handle that is held and controlled by a surgeon. These devices are generally lightweight and disposable.

A failing of current devices is the lack of control of the elongate electrosurgical member around its long axis at the insertion into the handle. It is most common that the elongate electrosurgical member rotates at least 15 to 30 degrees or more around the axis relative to a fixed face of the handle. This failing adversely affects the efficiency of the surgical procedure, creating undesirable delays and imprecision in the execution of the surgical manipulation of the tissue.

There is a need for adaptations to such surgical instrumentation to provide needed control on rotation of the elongate electrosurgical member.

BRIEF DESCRIPTION OF THE INVENTION

In an exemplary embodiment, an adapter for an electrosurgical instrument includes a socket and a stabilizer extending from the socket. The socket includes a mounting surface. The mounting surface includes a geometry arranged and disposed to accept a distal end of the electrosurgical instrument into the socket, and at least one retaining surface, the at least one retaining surface being arranged and disposed to interact with a conformation of the electrosurgical instrument when the socket is mounted onto the electrosurgical instrument such that the socket mounts non-rotatably onto the electrosurgical instrument. The stabilizer is arranged and disposed to engage with an elongate rotatable portion of the electrosurgical instrument when the socket is mounted onto the electrosurgical instrument. The stabilizer includes at least one stabilizing surface. The at least one stabilizing surface is arranged and disposed to be positioned adjacent to the elongate rotatable portion of the electrosurgical instrument at a plurality of points about the elongate rotatable portion of the electrosurgical instrument when the socket is mounted onto the electrosurgical instrument such that the elongate rotatable portion of the electrosurgical instrument is inhibited from rotating.

In another exemplary embodiment, an adapter for an electrosurgical instrument includes a socket and a stabilizer extending from the socket. The socket includes a mounting surface. The mounting surface includes a geometry arranged and disposed to accept a distal end of the electrosurgical instrument into the socket, and at least one retaining surface, the at least one retaining surface being arranged and disposed to interact with a conformation of the electrosurgical instrument when the socket is mounted onto the electrosurgical instrument such that the socket mounts non-rotatably onto the electrosurgical instrument. The stabilizer is arranged and disposed to engage with an elongate rotatable portion of the electrosurgical instrument when the socket is mounted onto the electrosurgical instrument. The stabilizer includes at least one stabilizing surface. The at least one stabilizing surface is arranged and disposed to be positioned adjacent to the elongate rotatable portion of the electrosurgical instrument at a plurality of points about the elongate rotatable portion of the electrosurgical instrument when the socket is mounted onto the electrosurgical instrument such that the elongate rotatable portion of the electrosurgical instrument is inhibited from rotating. When the socket is mounted onto the electrosurgical instrument, the elongate rotatable portion of the electrosurgical instrument retains between 0.1° to 5° of rotational freedom. The stabilizer includes two paddle members disposed on opposing sides of the elongate rotatable portion of the electrosurgical instrument when the socket is mounted onto the electrosurgical instrument. The geometry of the socket is arranged and disposed to accept a distal end of the electrosurgical instrument into the socket in a plurality of rotational orientations. The socket includes at least one lateral opening arranged and disposed to receive a control feature of the electrosurgical instrument such that when the socket is mounted onto the electrosurgical instrument in any one of the plurality rotational orientations, the control feature is accessible.

BRIEF DESCRIPTION OF THE DRAWINGS

Features and advantages of the general inventive concepts will become apparent from the following description made with reference to the accompanying drawings, including drawings represented herein in the attached set of figures, of which the following is a brief description:

FIG. 1 is a front perspective view of an exemplary electrosurgical instrument.

FIG. 2 is a rear perspective view of an adapter having one lateral opening for an electrosurgical instrument, according to an embodiment of the present disclosure.

FIG. 3 is a front perspective view of the adapter of FIG. 2, according to an embodiment of the present disclosure.

FIG. 4 is a rear view of the adapter of FIG. 2, according to an embodiment of the present disclosure.

FIG. 5 is a front view of the adapter of FIG. 2, according to an embodiment of the present disclosure.

FIG. 30 is a front perspective view of the adapter of FIG. 22 mounted on an electrosurgical instrument, according to an embodiment of the present disclosure.

FIG. 31 is a rear perspective view of the adapter of FIG. 22 mounted on an electrosurgical instrument, according to an embodiment of the present disclosure.

FIG. 32 is a cross-sectional view of the adapter of FIG. 22 along line 32-32, according to an embodiment of the present disclosure.

FIG. 33 is a cross-sectional view of the adapter of FIG. 30 along lines 33-33 mounted on an electrosurgical instrument, according to an embodiment of the present disclosure.

Figure 6:
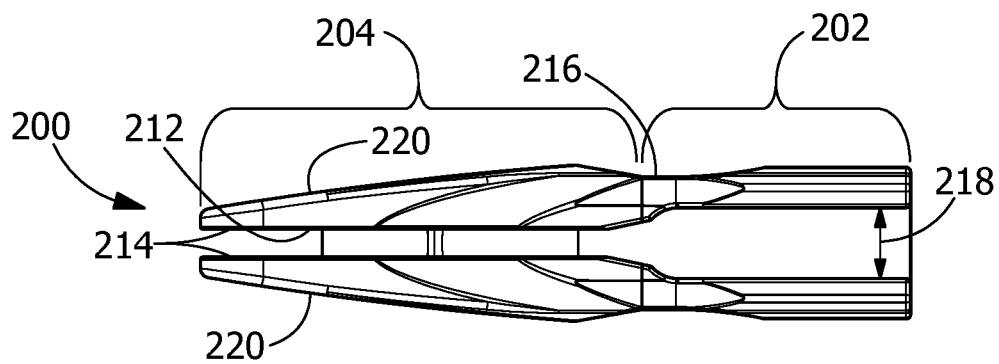
FIG. 6 is a top view of the adapter of FIG. 2, according to an embodiment of the present disclosure.
Figure 7:
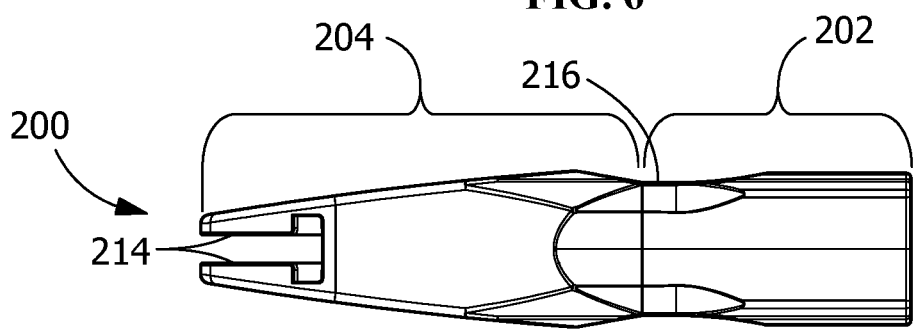
FIG. 7 is a bottom view of the adapter of FIG. 2, according to an embodiment of the present disclosure.
Figure 8:
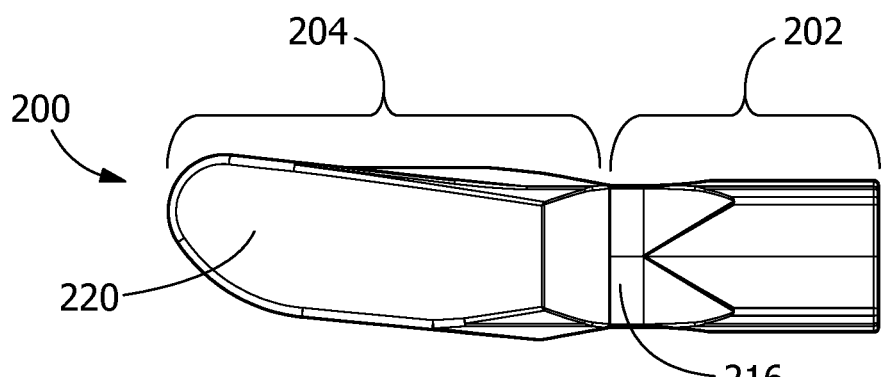
FIG. 8 is a right-side view of the adapter of FIG. 2, according to an embodiment of the present disclosure.
Figure 9:
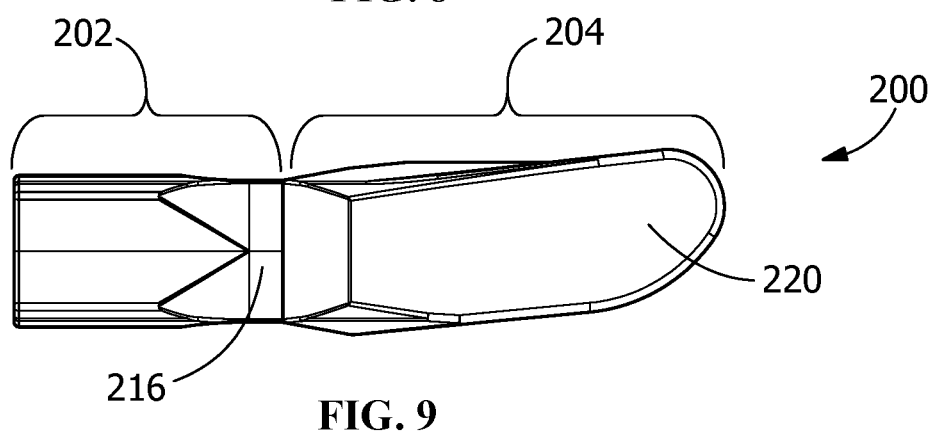
FIG. 9 is a left-side view of the adapter of FIG. 2, according to an embodiment of the present disclosure.
Figure 10:
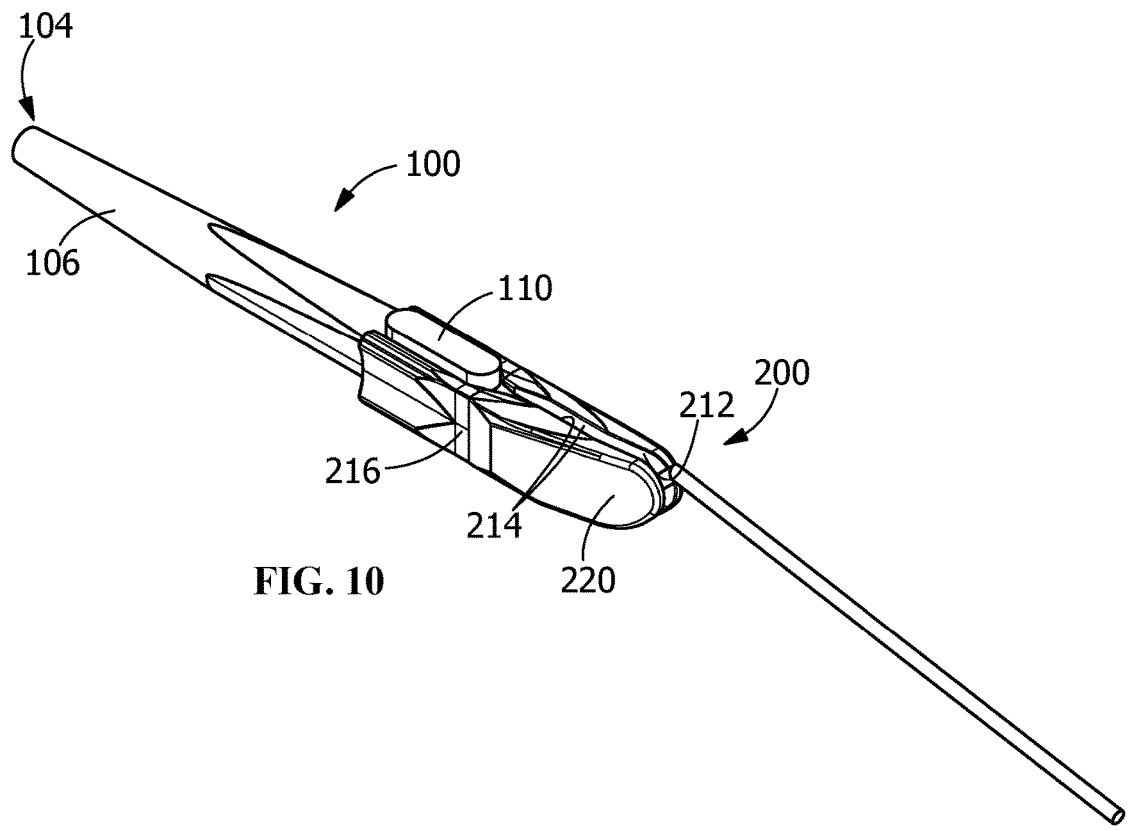
FIG. 10 is a front perspective view of the adapter of FIG. 2 mounted on an electrosurgical instrument, according to an embodiment of the present disclosure.
Figure 11:
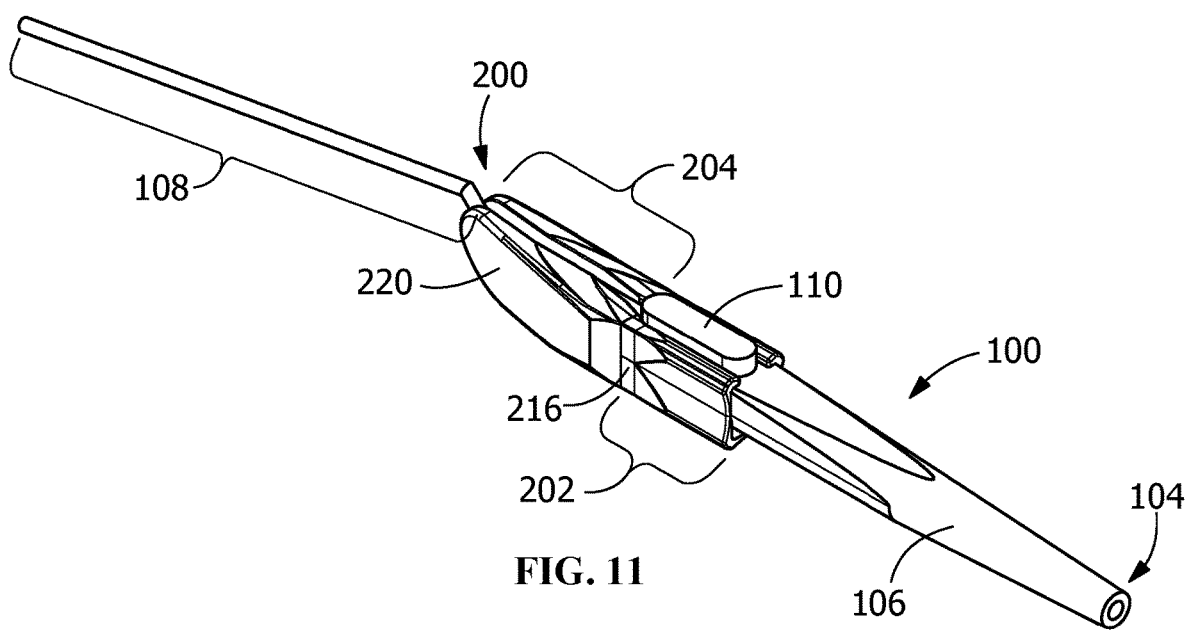
FIG. 11 is a rear perspective view of the adapter of FIG. 2 mounted on an electrosurgical instrument, according to an embodiment of the present disclosure.
Figure 12:
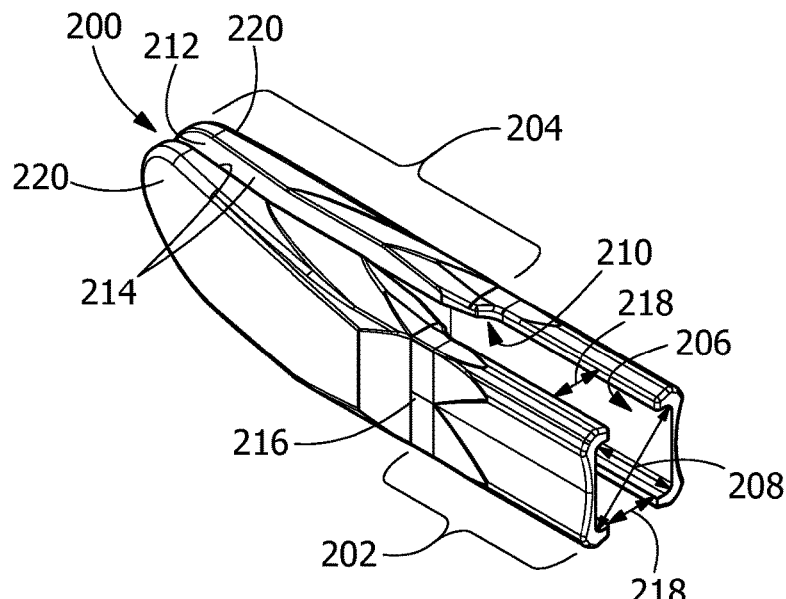
FIG. 12 is a rear perspective view of an adapter having two lateral openings for an electrosurgical instrument, according to an embodiment of the present disclosure.
Figure 13:
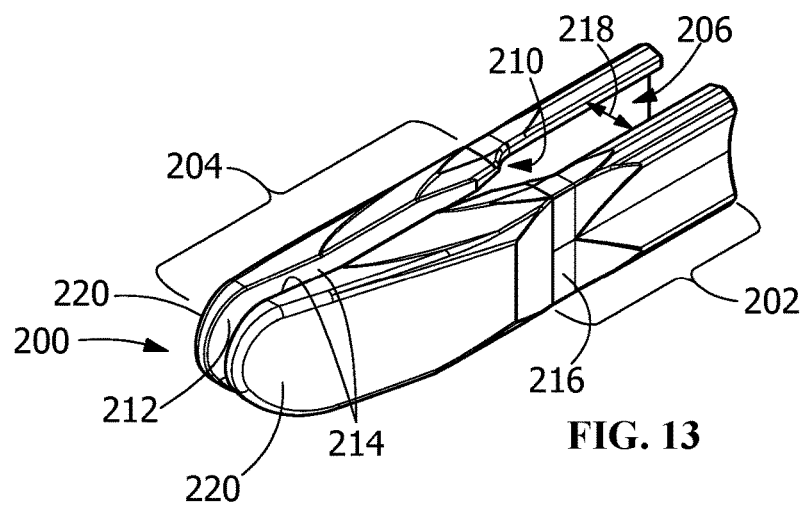
FIG. 13 is a front perspective view of the adapter of FIG. 12, according to an embodiment of the present disclosure.
Figure 14:
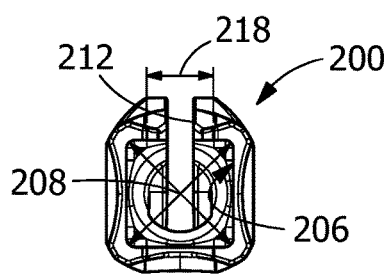
FIG. 14 is a rear view of the adapter of FIG. 12, according to an embodiment of the present disclosure.
Figure 15:
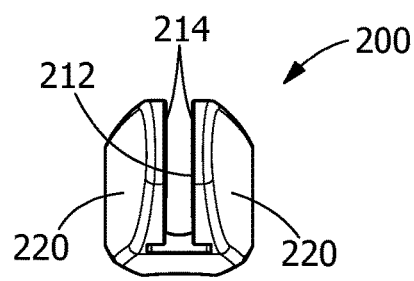
FIG. 15 is a front view of the adapter of FIG. 12, according to an embodiment of the present disclosure.
Figure 16:
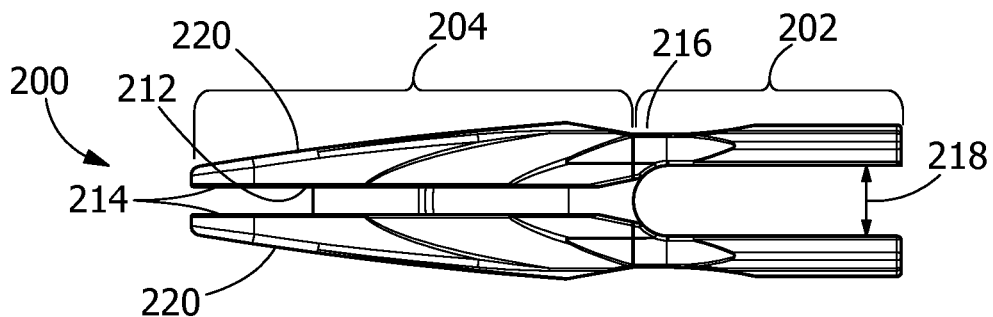
FIG. 16 is a top view of the adapter of FIG. 12, according to an embodiment of the present disclosure.
Figure 17:
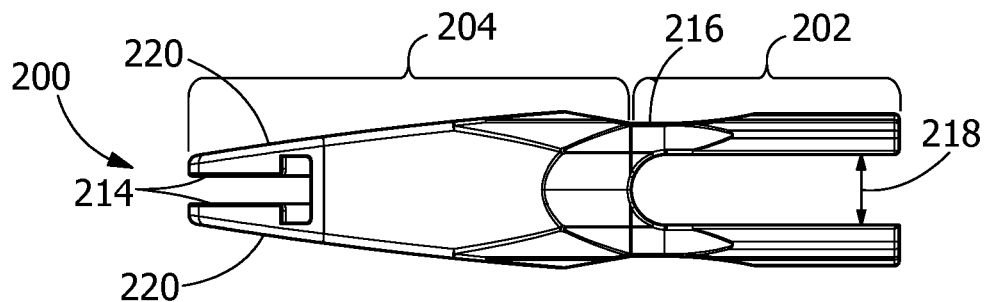
FIG. 17 is a bottom view of the adapter of FIG. 12, according to an embodiment of the present disclosure.
Figure 18:
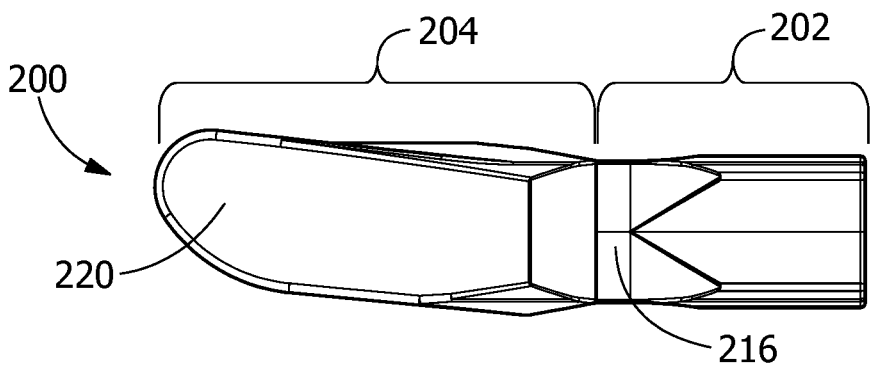
FIG. 18 is a right-side view of the adapter of FIG. 12, according to an embodiment of the present disclosure.
Figure 19:
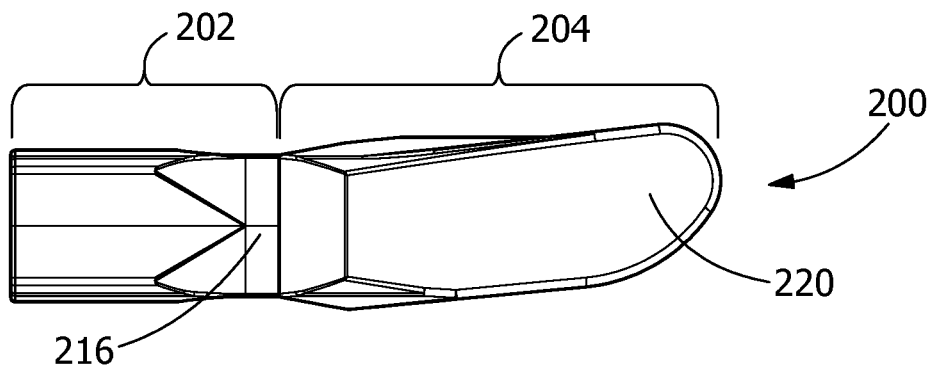
FIG. 19 is a left-side view of the adapter of FIG. 12, according to an embodiment of the present disclosure.
Figure 20:
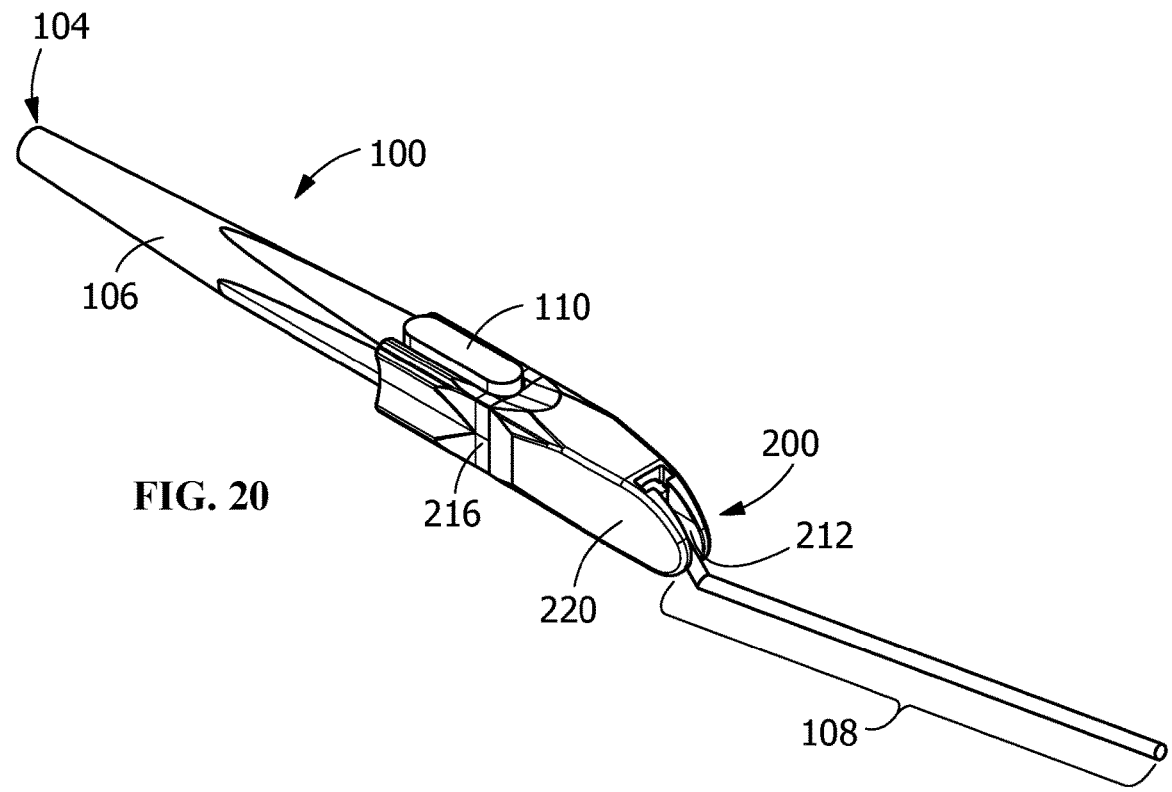
FIG. 20 is a front perspective view of the adapter of FIG. 12 mounted on an electrosurgical instrument, according to an embodiment of the present disclosure.
Figure 21:
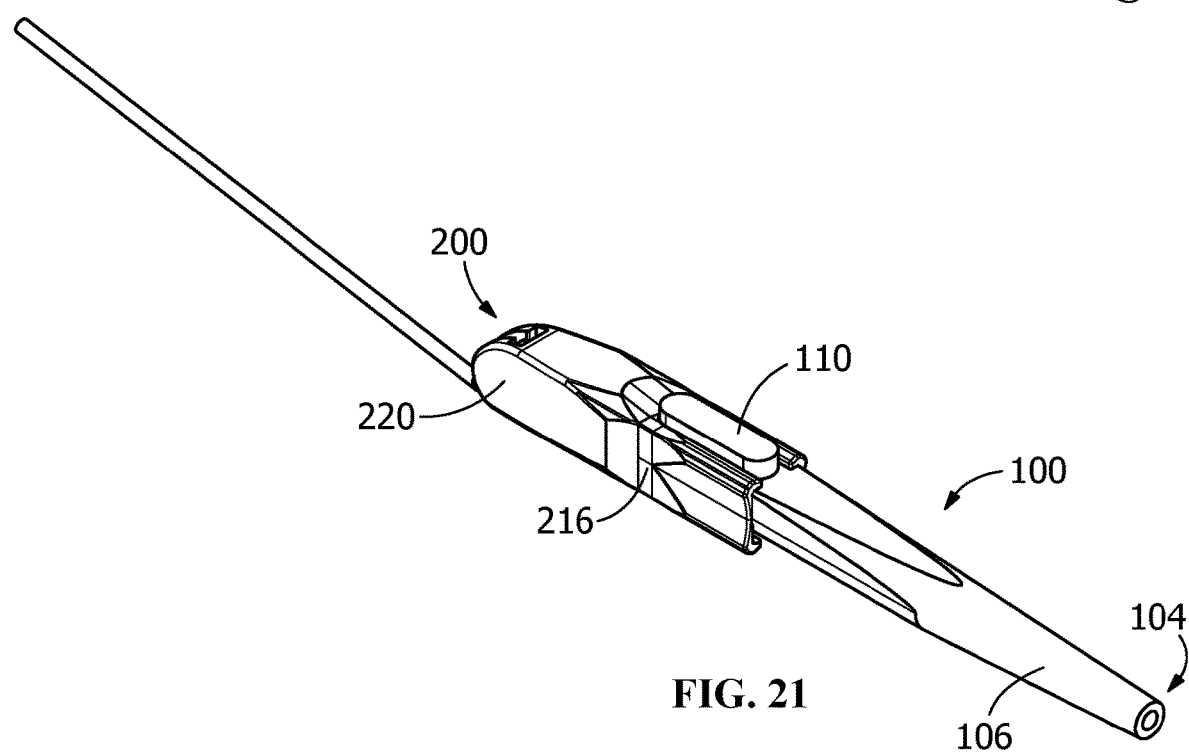
FIG. 21 is a rear perspective view of the adapter of FIG. 12 mounted on an electrosurgical instrument, according to an embodiment of the present disclosure.
Figure 22:
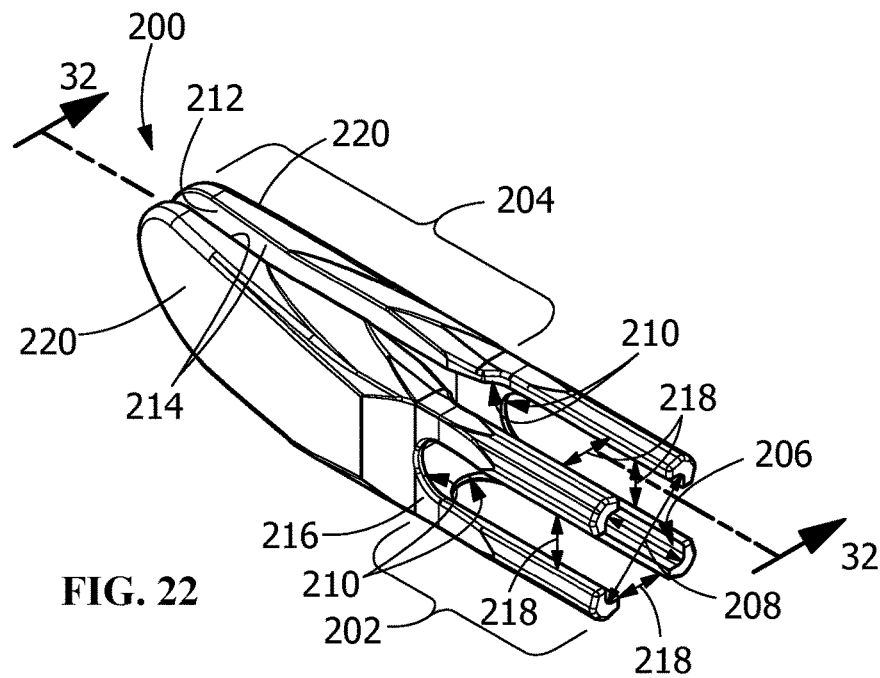
FIG. 22 is a rear perspective view of an adapter having four lateral openings for an electrosurgical instrument, according to an embodiment of the present disclosure.
Figure 23:
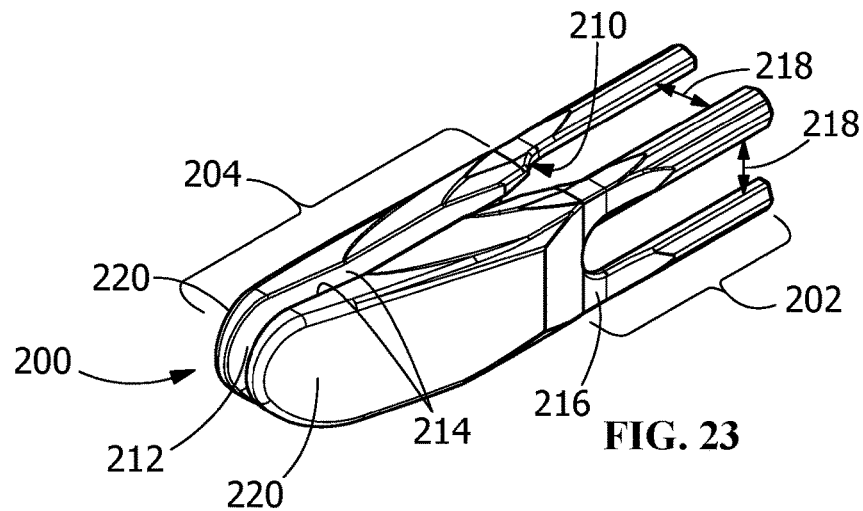
FIG. 23 is a front perspective view of the adapter of FIG. 22, according to an embodiment of the present disclosure.
Figure 24:
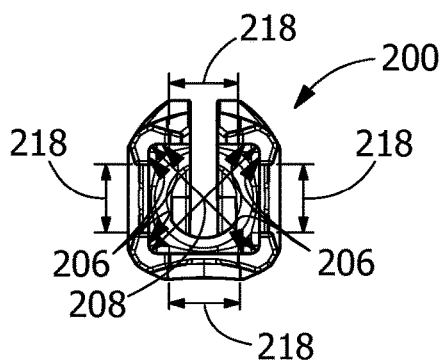
FIG. 24 is a rear view of the adapter of FIG. 22, according to an embodiment of the present disclosure.
Figure 25:
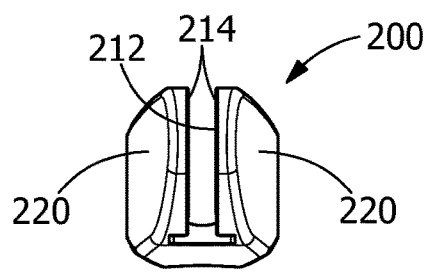
FIG. 25 is a front view of the adapter of FIG. 22, according to an embodiment of the present disclosure.
Figure 26:
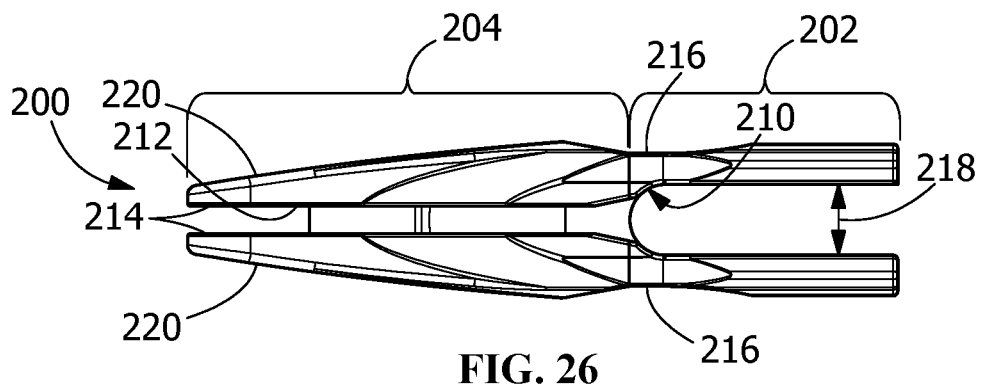
FIG. 26 is a top view of the adapter of FIG. 22, according to an embodiment of the present disclosure.
Figure 27:
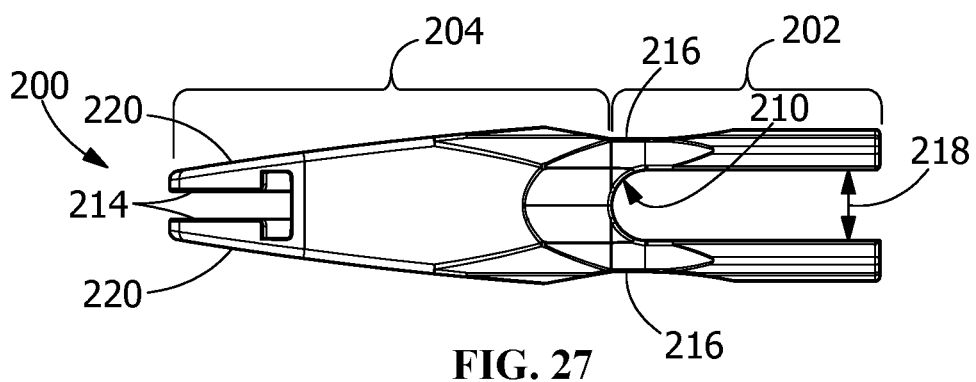
FIG. 27 is a bottom view of the adapter of FIG. 22, according to an embodiment of the present disclosure.
Figure 28:
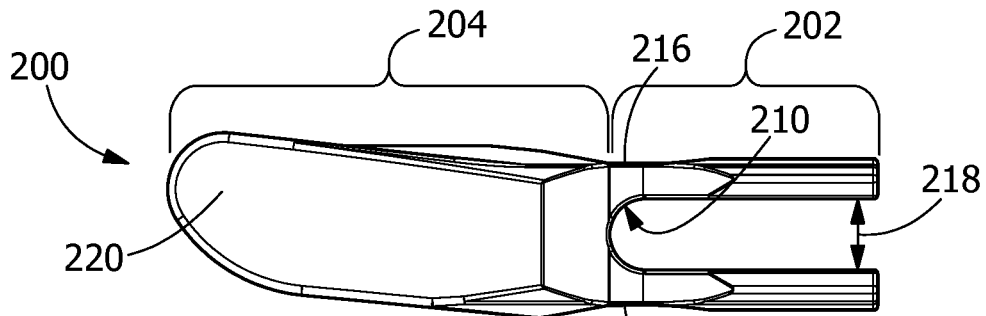
FIG. 28 is a right-side view of the adapter of FIG. 22, according to an embodiment of the present disclosure.
Figure 29:
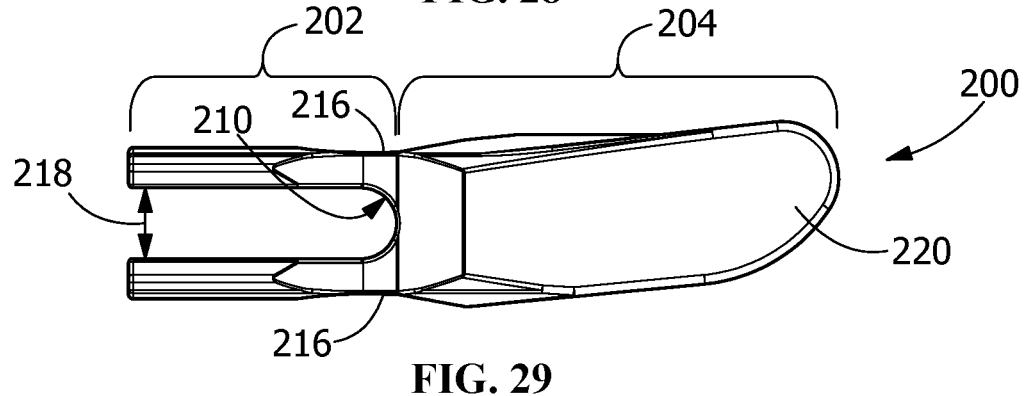
FIG. 29 is a left-side view of the adapter of FIG. 22, according to an embodiment of the present disclosure.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION

A surgical instrument adapter is provided for use in a wide variety of surgical procedures that include dissecting and retracting materials and tissue with an electrosurgical device such as a bovie during surgical procedures, the procedures performed either in open surgery or within a laparoscopic, arthroscopic or otherwise minimally invasive approach cavity.

As used herein, the singular forms "a," "an," and "the" are intended to include the plural forms as well, unless the context clearly indicates otherwise. The term "proximal" as used in connection with any object refers to the portion of the object that is closest to the operator of the object (or some other stated reference point), and the term "distal" refers to the portion of the object that is farthest from the operator of the object (or some other stated reference point). The term "operator" means and refers to any professional or paraprofessional who delivers clinical care to a medical patient, particularly in connection with the delivery of care.

Referring to FIG. 1, an electrosurgical instrument 100, such as a bovie, may include a distal end 102 and a proximal end 104, the portion of the electrosurgical instrument 100 from the distal end 102 to the proximal end 104 constituting a handle 106 of the electrosurgical instrument 100. The electrosurgical instrument 100 may also include an elongate rotatable portion 108 extending from the distal end 102 of the electrosurgical instrument 100, and may further include a control feature 110 disposed along the handle 106 of the electrosurgical instrument. The control feature 100 may be any suitable feature, including, but not limited to, a button (shown), a switch, a toggle, a contact sensor, or combinations thereof. In one embodiment, elongate rotatable portion 108 includes a length 112 between the distal end of the handle 106 and a bend 114.

Referring to FIGS. 2-37, in one embodiment, an adapter 200 for an electrosurgical instrument 100 includes a socket 202 and stabilizer 204. The socket 202 includes a mounting surface 206. The mounting surface 206 includes a geometry 208 and at least one retaining surface 210. The geometry 208 is arranged and disposed to accept a distal end 102 of the electrosurgical instrument 100 into the socket 202. The at least one retaining surface 210 is arranged and disposed to interact with a conformation 116 of the electrosurgical instrument 100 when the socket 202 is mounted onto the electrosurgical instrument 100 such that the socket 202 mounts non-rotatably onto the electrosurgical instrument 100. The stabilizer 204 extends from the socket 202 and is arranged and disposed to engage with an elongate rotatable portion 108 of the electrosurgical instrument 100 when the socket 202 is mounted onto the electrosurgical instrument 100. The stabilizer 204 includes at least one stabilizing surface 212 which is arranged and disposed to be positioned adjacent to the elongate rotatable portion 108 of the electrosurgical instrument 100 at a plurality of points 214 about the elongate rotatable portion 108 of the electrosurgical instrument 100 when the socket 202 is mounted onto the electrosurgical instrument 100 such that the elongate rotatable portion 108 of the electrosurgical instrument 100 is inhibited from rotating.

In one embodiment, when the socket 202 is mounted onto the electrosurgical instrument 100, the elongate rotatable portion 108 of the electrosurgical instrument 100 retains between 0.1° to 5° of rotational freedom, alternatively between 0.1° to 0.5°, alternatively between 0.25° to 0.75°, alternatively between 0.5° to 1°, alternatively between 0.75° to 1.25°, alternatively between 1° to 1.5°, alternatively between 1.25° to 1.75°, alternatively between 1.5° to 2°, alternatively between 1.75° to 2.25°, alternatively between 2° to 2.5°, alternatively between 2.25° to 2.75°, alternatively between 2.5° to 3°, alternatively between 2.75° to 3.25°, alternatively between 3° to 3.5°, alternatively between 3.25° to 3.75°, alternatively between 3.5° to 4°, alternatively between 3.75° to 4.25°, alternatively between 4° to 4.5°, alternatively between 4.25° to 4.75°, alternatively between 4.5° to 5°, or any combination or subrange thereof.

In an alternative embodiment, when the socket 202 is mounted onto the electrosurgical instrument 100, the elongate rotatable portion 108 of the electrosurgical instrument is essentially non-rotatable. As used herein, "essentially non-rotatable" indicates less than 0.1° of rotational freedom. In a further alternative embodiment, when the socket 202 is mounted onto the electrosurgical instrument 100, the elongate rotatable portion 108 of the electrosurgical instrument is non-rotatable.

As used herein, "rotational freedom" of the elongate rotatable portion 108 and characterization of the elongate rotatable portion 108 as being "non-rotatable" or "essentially non-rotatable" specifically refers to rotation or lack thereof of the elongate rotatable portion 108 as a whole relative to the electrosurgical instrument 100, and does not include torsion of the elongate rotatable portion 108 along its length.

Each of the socket 202 and stabilizer 204 is formed from any material that is suitable for medical devices, including, but not limited to, metal, plastic, and combinations thereof. Suitable plastic materials include, but are not limited to, food and/or surgical grade plastic that is sterilizable and non-conductive, and is semi-compliant, or non-compliant. In some embodiments, the material is selected from nylon, polyethylene, polyamide, polyether block amide (PEBAX), polyethylene terephthalate (PET), silicone poly octanediol-co-citrate (POC), polypropylene, polyether block (PBT), and combinations of these.

In one embodiment, the socket 202 and the stabilizer 204 are formed from the same material. In another embodiment, the socket 202 and the stabilizer 204 are formed from distinct materials.

The socket 202 may include a gripping surface 216. The gripping surface 216 may further include texturing (not shown).

Referring to FIGS. 2-11, in one embodiment the geometry 208 of the socket 202 is arranged and disposed to accept a distal end 102 of the electrosurgical instrument 100 into the socket 202 in a single rotational orientation.

Referring to FIGS. 12-31, in one embodiment the geometry 208 of the socket 202 is arranged and disposed to accept a distal end 102 of the electrosurgical instrument 100 into the socket 202 in a plurality of rotational orientations. FIGS. 12-21 depict an embodiment in which the geometry 208 of the socket 202 is arranged and disposed to accept a distal end 102 of the electrosurgical instrument 100 into the socket 202 in two rotational orientations. FIGS. 22-31 depict an embodiment in which the geometry 208 of the socket 202 is arranged and disposed to accept a distal end 102 of the electrosurgical instrument 100 into the socket 202 in four rotational orientations. However, the adapter 200 may be configured such that the socket 202 is arranged and disposed to accept a distal end 102 of the electrosurgical instrument 100 into the socket 202 in any suitable number of rotational orientations, further including, but not limited to, three rotational orientations, at least four rotational orientations, five rotational orientation, or six rotational orientations.

Referring to FIGS. 2-11, in one embodiment the socket 202 includes at least one lateral opening 218 arranged and disposed to receive a control feature 110 of the electrosurgical instrument 100 such that when the socket 202 is mounted onto the electrosurgical instrument 100, the control feature 110 is accessible to a person holding the electrosurgical instrument 100.

Referring to FIGS. 12-31, in one embodiment the socket 202 includes a plurality of lateral openings 218 arranged and disposed to receive a control feature 110 of the electrosurgical instrument 100 such that when the socket 202 is mounted onto the electrosurgical instrument 100 in any one of a plurality rotational orientations, the control feature 110 is accessible to a person holding the electrosurgical instrument 100. FIGS. 12-21 depict an embodiment in which the socket 202 includes two lateral openings 218 arranged and disposed to receive a control feature 110 of the electrosurgical instrument 100 such that when the socket 202 is mounted onto the electrosurgical instrument 100 in either of two rotational orientations, the control feature 110 is accessible to a person holding the electrosurgical instrument 100. FIGS. 22-31 depict an embodiment in which the socket 202 includes four lateral openings 218 arranged and disposed to receive a control feature 110 of the electrosurgical instrument 100 such that when the socket 202 is mounted onto the electrosurgical instrument 100 in any one of four rotational orientations, the control feature 110 is accessible to a person holding the electrosurgical instrument 100. However, the adapter 200 may be configured such that the socket 202 includes any suitable number of lateral openings 218 arranged and disposed to receive a control feature 110 of the electrosurgical instrument 100 such that when the socket 202 is mounted onto the electrosurgical instrument 100 in any number of rotational orientations, the control feature 110 is accessible to a person holding the electrosurgical instrument 100, further including, but not limited to, three rotational orientations, at least four rotational orientations, five rotational orientation, or six rotational orientations.

Referring to FIGS. 2-33 and 36-37, in one embodiment, the socket 202 and the stabilizer 204 are a unitary and continuous article. As used herein, "unitary and continuous" indicates the absence of a joint between the socket 202 and the stabilizer 204, expressly including, but not limited to, a mechanical joint, a braze joint, a weld joint, and an adhesive joint.

Figure 34:
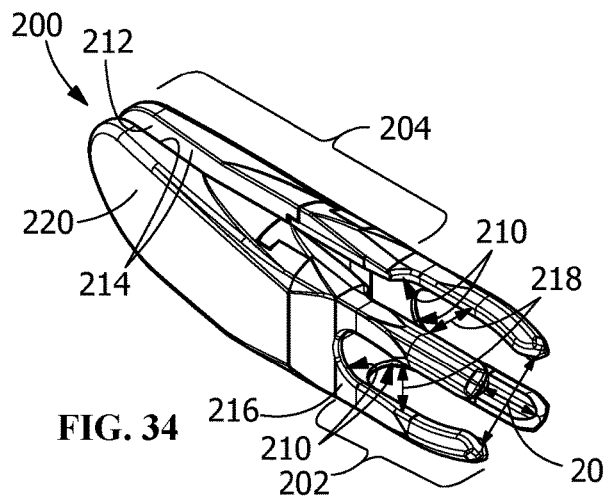
FIG. 34 is rear perspective view of a two-piece adapter for an electrosurgical instrument, according to an embodiment of the present disclosure.
Figure 35:
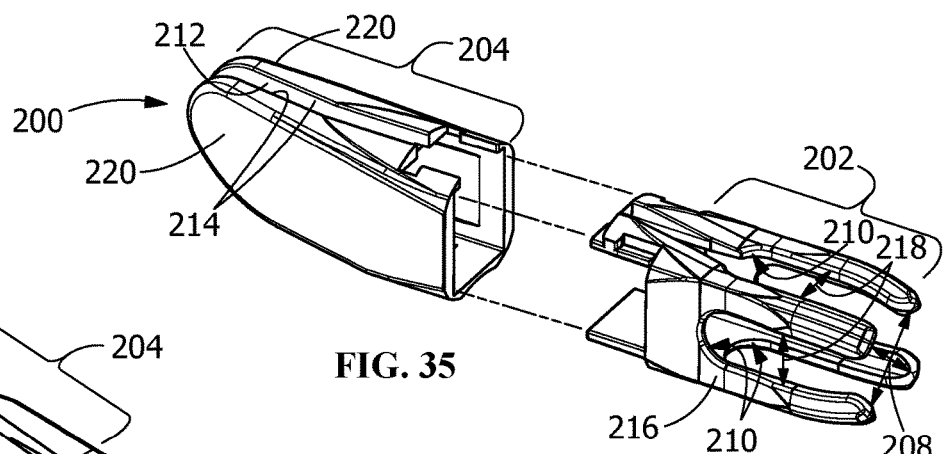
FIG. 35 is rear perspective view of the two-piece adapter of FIG. 34 in a disassembled state, according to an embodiment of the present disclosure.

Referring to FIGS. 34-35, in another embodiment, the stabilizer 204 is reversibly attached to the socket 202. As used herein, "reversibly attached" indicates that the stabilizer 204 and the socket 202 are separable from one another without damaging either the stabilizer 204 or the socket 202. In a further embodiment, the stabilizer 204 may be reversibly attached to the socket in a single rotational orientation, alternatively in a plurality of rotational orientations, alternatively in at least three rotational orientations, alternatively in at least four rotational orientations, alternatively in at least five rotational orientations, alternatively in at least six rotational orientations.

Referring to FIGS. 10, 11, 20, 21, 30, 31, and 33, in one embodiment, the stabilizer 204 extends from the socket 202 for less than a length 112 along the elongate rotational portion 108 of the electrosurgical instrument 100 at which the elongate rotatable portion 108 of the electrosurgical instrument 100 bends 114 when the socket 202 is mounted onto the electrosurgical instrument 100. In an alternate embodiment (not shown), the stabilizer 204 extends from the socket 202 for at least the length 112 along the elongate rotational portion 108 of the electrosurgical instrument 100 at which the elongate rotatable portion 108 of the electrosurgical instrument 100 bends 114 when the socket 202 is mounted onto the electrosurgical instrument. The stabilizer 204 extending from the socket 202 for at least the length 112 along the elongate rotational portion 108 of the electrosurgical instrument 100 at which the elongate rotatable portion 108 of the electrosurgical instrument 100 bends may interfere with, reduce, and/or prevent flexion of the elongate electrosurgical member 108 off its long axis and thus further stabilize the elongate electrosurgical member 108 for enhanced control and precision during tissue manipulation.

Referring to FIGS. 2-35, in one embodiment, the stabilizer 204 includes two paddle members 220 disposed on opposing sides of the elongate rotatable portion 108 of the electrosurgical instrument 100 when the socket 202 is mounted into the electrosurgical instrument 100.

Figure 36:
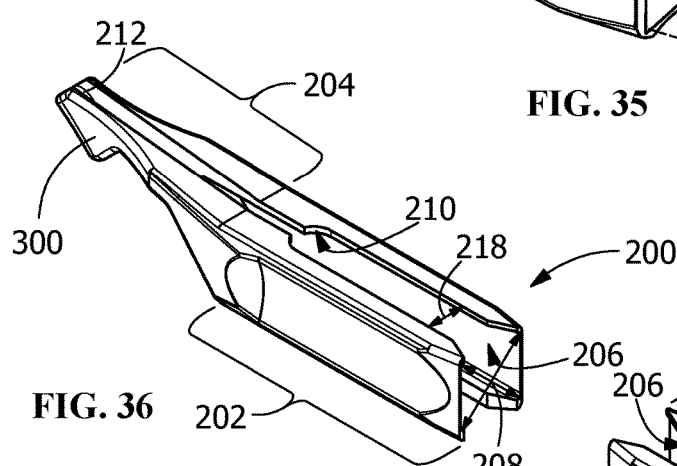
FIG. 36 is a rear perspective view of an adapter having a cradle member for an electrosurgical instrument, according to an embodiment of the present disclosure.
Figure 37:
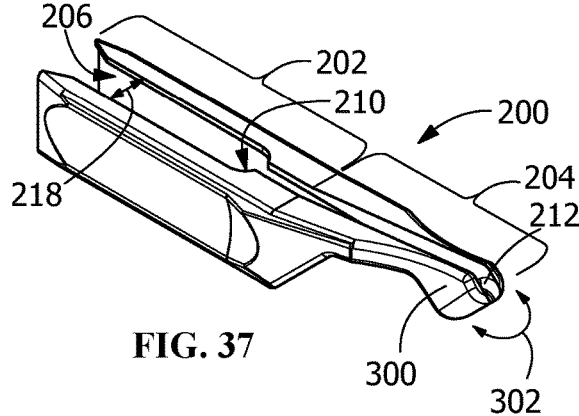
FIG. 37 is a front perspective view of the adapter of FIG. 36, according to an embodiment of the present disclosure.

Referring to FIGS. 36-37, in another embodiment, the stabilizer 204 includes a cradle member 300, and the at least one stabilizing surface 212 at the cradle member 300 is continuously adjacent to the elongate rotatable portion 108 of the electrosurgical instrument 100 over an arc 302 of at least 90° when the socket 202 is mounted onto the electrosurgical instrument 100. The at least one stabilizing surface 212 over the arc 302 of at least 90° may include any suitable conformation, including, but not limited to, a u-shaped conformation 304, a v-shaped conformation (not shown), and combinations thereof, when the socket 202 is mounted onto the electrosurgical instrument 100.

In one embodiment, the cradle member 300 is arranged and disposed to be in continuous contact with the elongate rotatable portion 108 of the electrosurgical instrument 100 over the arc 302 of at least 90° when the socket 202 is mounted onto the electrosurgical instrument 100.

In another embodiment, the cradle member 300 is arranged and disposed to be in separated from the elongate rotatable portion 108 of the electrosurgical instrument 100 over the arc 302 of at least 90° other than at two points 214 when the socket 202 is mounted onto the electrosurgical instrument 100.

In one embodiment, the at least one stabilizing surface 212 at the cradle member 300 is continuously adjacent to the elongate rotatable portion 108 of the electrosurgical instrument 100 over an arc 302 of at least 100° when the socket 202 is mounted onto the electrosurgical instrument 100, alternatively over an arc 302 of at least 110°, alternatively over an arc 302 of at least 120°, alternatively over an arc 302 of at least 130°, alternatively over an arc 302 of at least 140°, alternatively over an arc 302 of at least 150°, alternatively over an arc 302 of at least 160°, alternatively over an arc 302 of at least 170°, alternatively over an arc 302 of at least 180°, alternatively over an arc 302 of at least 190°, alternatively over an arc 302 of at least 200°, alternatively over an arc 302 of at least 210°, alternatively over an arc 302 of at least 220°, alternatively over an arc 302 of at least 230°, alternatively over an arc 302 of at least 240°, alternatively over an arc 302 of at least 250°, alternatively over an arc 302 of at least 260°, alternatively over an arc 302 of at least 270°.

In one embodiment, the cradle member 300 includes a rigid arc, ring, or radiused arc with opposing extensions that are transverse to an axis of rotation of the elongate rotatable portion 108 of the electrosurgical instrument 100.

Embodiments of the present invention are not in any way limited in use for any particular type of surgery, and thus, may be use in nonlimiting examples that include cosmetic, general surgical, within the brain, the bone extremities, in the pelvis and abdomen, and in the spine, and in any mode of access, including, but not limited to direct surgical approaches, and minimally invasive approaches. In some specific examples as used in the context of spinal surgery, embodiments of the invention may be used in surgical approaches including direct, oblique or posterior-lateral, anterior (ALIF), posterior (PLIF), transverse (TLIF), lateral, and extreme lateral (XLIF), as well as in any other surgeries in the body, including.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, devices and components, alternatives as to form, fit and function, and so on) may be described herein, such descriptions are not intended to be a complete or exhaustive list of available alternative embodiments, whether presently known or later developed.

Those skilled in the art may readily adopt one or more of the inventive aspects, concepts and features into additional embodiments and uses within the scope of the general inventive concepts, even if such embodiments are not expressly disclosed herein. Additionally, even though some features, concepts and aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated.

Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

What is claimed is:

1. An adapter for an electrosurgical instrument, comprising:
   a socket including a mounting surface, the mounting surface including:
      a geometry arranged and disposed to accept a distal end of the electrosurgical instrument into the socket; and
      at least one retaining surface, the at least one retaining surface being arranged and disposed to interact with a conformation of the electrosurgical instrument when the socket is mounted onto the electrosurgical instrument such that the socket mounts non-rotatably onto the electrosurgical instrument; and a stabilizer extending from the socket, the stabilizer being arranged and disposed to engage with an elongate rotatable portion of the electrosurgical instrument when the socket is mounted onto the electrosurgical instrument, the stabilizer including at least one stabilizing surface, the at least one stabilizing surface being arranged and disposed to be positioned adjacent to the elongate rotatable portion of the electrosurgical instrument at a plurality of points about the elongate rotatable portion of the electrosurgical instrument when the socket is mounted onto the electrosurgical instrument such that the elongate rotatable portion of the electrosurgical instrument is inhibited from rotating.

2. The adapter of claim 1, wherein when the socket is mounted onto the electrosurgical instrument, the elongate rotatable portion of the electrosurgical instrument retains between 0.1° to 5° of rotational freedom.

3. The adapter of claim 1, wherein when the socket is mounted onto the electrosurgical instrument, the elongate rotatable portion of the electrosurgical instrument is non-rotatable.

4. The adapter of claim 1, wherein the stabilizer includes two paddle members disposed on opposing sides of the elongate rotatable portion of the electrosurgical instrument when the socket is mounted onto the electrosurgical instrument.

5. The adapter of claim 1, wherein the stabilizer includes a cradle member, and the at least one stabilizing surface at the cradle member is continuously adjacent to the elongate rotatable portion of the electrosurgical instrument over an arc of at least 90° when the socket is mounted onto the electrosurgical instrument.

6. The adapted of claim 5, wherein the at least one stabilizing surface over the arc of at least 90° includes a u-shaped conformation when the socket is mounted onto the electrosurgical instrument.

7. The adapted of claim 5, wherein the at least one stabilizing surface over the arc of at least 90° includes a v-shaped conformation when the socket is mounted onto the electrosurgical instrument.

8. The adapter of claim 5, the cradle member is arranged and disposed to be in continuous contact with the elongate rotatable portion of the electrosurgical instrument over an arc of at least 90° when the socket is mounted onto the electrosurgical instrument.

9. The adapter of claim 5, wherein the at least one stabilizing surface at the cradle member is continuously adjacent to the elongate rotatable portion of the electrosurgical instrument over an arc of at least 120° when the socket is mounted onto the electrosurgical instrument.

10. The adapter of claim 5, wherein the cradle member includes a rigid arc, ring, or radiused arc with opposing extensions that are transverse to an axis of rotation of the elongate rotatable portion of the electrosurgical instrument.

11. The adapter of claim 1, wherein the socket is formed of plastic selected form the group consisting of elastomeric plastic, silicone, and combinations thereof.

12. The adapter of claim 11, wherein the plastic comprises nylon.

13. The adapter of claim 1, wherein the socket and the stabilizer are formed of a same material.

14. The adapter of claim 1, wherein the socket further includes a gripping surface having texturing.

15. The adapter of claim 1, wherein the stabilizer extends from the socket for at least a length along the elongate rotatable portion of the electrosurgical instrument at which the elongate rotatable portion of the electrosurgical instrument bends, when the socket is mounted onto the electrosurgical instrument.

16. The adapter of claim 1, wherein the geometry of the socket is arranged and disposed to accept a distal end of the electrosurgical instrument into the socket in a single rotational orientation.

17. The adapter of claim 1, wherein the socket includes a plurality of lateral openings arranged and disposed to receive a control feature of the electrosurgical instrument such that when the socket is mounted onto the electrosurgical instrument in any one of a plurality rotational orientations, the control feature is accessible.

18. The adapter of claim 1, wherein the socket and the stabilizer are a unitary and continuous article.

19. The adapter of claim 1, wherein the stabilizer is reversibly attached to the socket.

20. An adapter for an electrosurgical instrument, comprising:
a socket including a mounting surface, the mounting surface including:
a geometry arranged and disposed to accept a distal end of the electrosurgical instrument into the socket; and
at least one retaining surface, the at least one retaining surface being arranged and disposed to interact with a conformation of the electrosurgical instrument when the socket is mounted onto the electrosurgical instrument such that the socket mounts non-rotatably onto the electrosurgical instrument; and
a stabilizer extending from the socket, the stabilizer being arranged and disposed to engage with an elongate rotatable portion of the electrosurgical instrument when the socket is mounted onto the electrosurgical instrument, the stabilizer including at least one stabilizing surface, the at least one stabilizing surface being arranged and disposed to be positioned adjacent to the elongate rotatable portion of the electrosurgical instrument at a plurality of points about the elongate rotatable portion of the electrosurgical instrument when the socket is mounted onto the electrosurgical instrument such that the elongate rotatable portion of the electrosurgical instrument is inhibited from rotating,
wherein when the socket is mounted onto the electrosurgical instrument, the elongate rotatable portion of the electrosurgical instrument retains between 0.1° to 5° of rotational freedom,
wherein the stabilizer includes two paddle members disposed on opposing sides of the elongate rotatable portion of the electrosurgical instrument when the socket is mounted onto the electrosurgical instrument,
wherein the geometry of the socket is arranged and disposed to accept a distal end of the electrosurgical instrument into the socket in a plurality of rotational orientations,
wherein the socket includes at least one lateral opening arranged and disposed to receive a control feature of the electrosurgical instrument such that when the socket is mounted onto the electrosurgical instrument in any one of the plurality rotational orientations, the control feature is accessible.

* * * * *